(12) United States Patent
Gilbert (10) Patent No.: US 6,808,683 B2
(45) Date of Patent: Oct. 26, 2004

(54) DROPLET DISPENSING SYSTEM

(75) Inventor: John Gilbert, Brookline, MA (US)

(73) Assignee: Cytonome, Inc., Watertown, MA (US)

(*) Notice: Subject to any disclaimer, the term of this patent is extended or adjusted under 35 U.S.C. 154(b) by 77 days.

(21) Appl. No.: 10/029,108

(22) Filed: Dec. 21, 2001

(65) Prior Publication Data

US 2003/0059949 A1 Mar. 27, 2003

Related U.S. Application Data

(60) Provisional application No. 60/325,040, filed on Sep. 25, 2001.

(51) Int. Cl.[7] .............................. G01N 35/10; B41J 2/14
(52) U.S. Cl. ........................ 422/100; 422/99; 436/180; 347/47; 347/54; 347/85
(58) Field of Search .................... 422/99, 100; 436/180; 347/47, 54, 85

(56) References Cited

U.S. PATENT DOCUMENTS

| | | | |
|---|---|---|---|
| 5,474,796 A | 12/1995 | Brennan | 427/2.13 |
| 5,658,802 A | 8/1997 | Hayes et al. | 436/518 |
| 5,741,554 A | 4/1998 | Tisone | 427/424 |
| 5,927,547 A | 7/1999 | Papen et al. | 222/57 |
| 5,958,342 A | 9/1999 | Gamble et al. | 422/100 |
| 6,001,309 A | 12/1999 | Gamble et al. | 422/100 |
| 6,024,925 A | 2/2000 | Little et al. | 422/100 |
| 6,028,189 A | 2/2000 | Blanchard | 536/25.3 |
| 6,066,297 A | 5/2000 | Torti et al. | 422/100 |
| 6,101,946 A | 8/2000 | Martinsky | 101/494 |
| 6,133,044 A | 10/2000 | Van den Engh | 436/177 |
| 6,218,193 B1 | 4/2001 | Kraft et al. | 436/180 |
| 6,221,653 B1 | 4/2001 | Caren et al. | 435/287.2 |
| 6,232,129 B1 | 5/2001 | Wiktor | 436/180 |
| 6,296,452 B1 | 10/2001 | Caren | 417/53 |
| 6,351,274 B1 | 2/2002 | Hawkins et al. | 346/140.1 |
| 6,364,460 B1 | 4/2002 | Sager | 347/54 |
| 6,405,609 B1 | 6/2002 | Richards et al. | 73/864.14 |

OTHER PUBLICATIONS

Önnerfjord, P. et al. "Picoliter Sample Preparation in MALDI–TOF MS Using a Micromachined Silicon Flow–Through Dispenser" *Anal. Chem.* 70(22):4755–4760 (Nov. 15, 1998).

*Primary Examiner*—Jan M. Ludlow
(74) *Attorney, Agent, or Firm*—Lahive & Cockfield, LLP.; Anthony A. Laurentano; Elizabeth A. Hanley (57) ABSTRACT

A droplet dispensing system for forming and dispensing droplets of a liquid sample is provided. The droplet dispensing system is fabricated on the tip of a dispensing pin. The tip of the dispensing pin includes a droplet ejection nozzle, a filling channel, a chamber and an actuator for ejecting droplets on demand. The system further includes a holder for mounting the dispensing pin. The holder also contains a control circuit for activating the actuator.

25 Claims, 4 Drawing Sheets

DROPLET DISPENSING SYSTEM

This application claims priority to U.S. Provisional Patent Application No. 60/325,040, entitled "Droplet Dispensing System" filed Sep. 25, 2001, and is related to U.S. patent application Ser. No. 10/028,852, entitled "Microfluidic System Including a Virtual Wall Fluid Interface Port for Interfacing Fluids with the Microfluidic System", filed Jun. 20, 2002. U.S. patent application Ser. No. 10/027,484, entitled "Microfludic System Including a Virtual Wall Fluid Interface Port for Interfacing Fluids with the Microfluidic System", filed Jun. 20, 2002. U.S. patent application Ser. No. 10/027,516, entitled "Microfluidic System Including a Virtual Wall Fluid Interface Port for Interfacing Fluids with the Microfluidic System", filed Jun. 20, 2002; U.S. patent application Ser. No. 10/027,171, entitled "Microfabricated Two-Pin Liquid Sample Dispensing System", filed Jun. 20, 2002; and U.S. patent application Ser. No. 10/027,922, entitled "Small Molecule Substrate Based Enzyme Activity Assays", filed Jun. 20, 2002. The contents of the foregoing patent applications are herein incorporated by reference. The contents of all references, issued patents, or published patent applications cited herein are expressly incorporated by reference.

FIELD OF THE INVENTION

The present invention relates to a liquid dispensing system for forming and dispensing droplets of a liquid sample.

BACKGROUND OF THE INVENTION

Many chemical, biomedical, bioscience and pharmaceutical industries require chemical operations, such as reactions, separations and subsequent detection steps, to be performed on samples. It is generally desirable to introduce these samples into a sample handling system, such as a microfluidic system capable of handling and analyzing chemical and biological specimens, quickly, efficiently and in a highly controllable manner.

Many methods have been described for the interfacing of fluids, e.g., samples, analytes, reagents, precursors for synthesis and buffers, towards, within or between microfluidic systems. Generally, introduction of a liquid sample to a microfluidic system is accomplished through sample channels or sample wells. To introduce a liquid sample to the microfluidic system, a capillary tube may be provided, which dispenses a liquid sample to a sample well, sample channel or other sample introduction port. A significant drawback of using a capillary tube concerns the low injection efficiency inherent to capillary tubes, that is, the ratio between the volume of liquid required for a particular chemical operation in a part of the microfluidic system, and the total volume of liquid required for the introductory operation. Moreover, it is generally difficult to control the precise volume of dispensed sample using capillary tubes. Furthermore, capillary tubes are subject to contamination, because the same port used to fill the tube is also used to eject the liquid sample.

U.S. Pat. No. 6,101,946 of Martinsky describes a pin-based system for printing microarrays of biochemical substances. The microarray printing system comprises a printing pin having a sample channel and a flat tip. The pin applies a biochemical substance by filling the sample channel and subsequently directly contacting a printing substrate, to deliver the sample from the sample channel to the printing substrate. A drawback of the pin-based system described in the '946 patent concerns the ability to control the amount of delivered sample. The pin-based system is subject to contamination and breakage, because it requires direct contact between the pin tip and the printing substrate. Another drawback concerns the difficulty of precisely positioning the tip of the pin to provide sufficient contact to result in delivery of a sample.

U.S. Pat. No. 6,110,426 of Shalon et al., the contents of which are herein incorporated by reference, describes a capillary dispenser for forming microarrays of biological samples. The capillary dispenser comprises an elongate open capillary channel adapted to hold a liquid sample. The channel is formed by a pair of spaced-apart, coextensive, elongate members, which are tapered toward one another and converge at a tip region at the lower end of the channel. The elongate members are fixed relative to each other and the capillary channel is limited to a fixed volume. Furthermore, it is difficult to control the amount of sample that is acquired and dispensed from the capillary dispenser of the '246 patent.

SUMMARY OF THE INVENTION

The present invention provides a droplet dispensing system which forms and dispenses droplets of a liquid sample on demand. The droplet dispensing system comprises a holder and one or more dispensing pins. Each dispensing pin has a tip for forming and ejecting droplets of a liquid sample from a supply of liquid sample stored in the tip. The tip of each dispensing pin includes a droplet ejection nozzle for controllably and selectively ejecting a droplet of liquid from the tip of the dispensing pin. Each dispensing pin tip includes a sample chamber in fluid communication with the ejection nozzle for holding a supply of a liquid sample. The tip further includes a filling channel in fluid communication with the sample chamber for filling the tip with a predetermined volume of liquid sample from a reservoir. An actuator is located on the tip adjacent to the ejection nozzle and communicates with the sample chamber. The droplet dispensing system forms and ejects droplets through the ejection nozzle by activating the actuator.

A method of manufacturing a dispensing system is also provided. According to the illustrative embodiment, the droplet dispensing system is fabricated from a silicon wafer. A photolithography process is utilized to etch the filling channel, sample chamber and ejection nozzle in the tip of a dispensing pin. A suitable actuator is attached to the tip to provide for formation and ejection of droplets from the ejection nozzle.

The droplet dispensing system provides fast and flexible filling of a predetermined amount of liquid sample in the dispensing system via the tip of a dispensing pin. The droplet dispensing system provides efficient and rapid dispensing of the liquid sample from the tip of a dispensing pin in the form of droplets having a precisely controlled volume. The droplet dispensing system enhances liquid sample application by improving efficiency, speed and controllability, while reducing waste and contamination.

According to one aspect a droplet dispensing system comprising a dispensing pin is provided. The sample dispensing system comprises a dispensing pin having a tip. The tip includes a sample chamber, a sample filling channel formed in the tip and in fluid communication with the sample chamber for loading a liquid sample into the sample chamber a droplet ejection nozzle in fluid communication with the sample chamber for ejecting a droplet of the liquid sample from the sample chamber and an actuator located adjacent to the sample chamber for forming the droplet.

According to another aspect, a droplet dispensing system comprises two interacting pins is provided. The two-pin droplet dispensing system comprises a first pin and a dispensing pin positioned in proximity to each other to form a filling channel therebetween. The dispensing pin has a tip further comprising a sample chamber located in fluid communication with the sample filling channel, an ejection nozzle for ejecting a droplet from the sample chamber and an actuator for triggering formation and ejection of a droplet from the ejection nozzle.

According to yet another aspect, a method of dispensing a liquid sample is provided. The method of dispensing a liquid sample comprises providing a droplet dispensing system comprising a pin having a tip including filling channel for filling the tip with a predetermined volume of liquid sample, a sample chamber, an ejection nozzle and an actuator for effecting formation of a droplet. The method further comprises the step of activating the actuator to produce a droplet of liquid sample at the sample ejection nozzle.

According to another aspect, a liquid sample dispensing system, comprising a holder and an array of dispensing pins connected to the holder is provided. Each dispensing pin in the array has a tip and a sample chamber formed in the tip for holding a predetermined volume of sample, a sample filling channel formed in the tip and in fluid communication with the sample chamber for loading a liquid sample into the sample chamber and a droplet ejection nozzle in fluid communication with the sample chamber for ejecting a droplet of the liquid sample from the sample chamber. The liquid sample dispensing system further includes an actuator coupled to the sample chamber of one or more of the dispensing pins for forming one or more droplets upon activation of the actuator.

DETAILED DESCRIPTION OF THE ILLUSTRATIVE EMBODIMENT

The present invention provides a droplet dispensing system for forming and dispensing liquid droplets of a sample for fluidic systems. The droplet dispensing system of the present invention provides precise sample uptake and delivery of a liquid sample to a sample handling system in the form of sub-micron-sized droplets. The droplet dispensing system is suitable for use in a basic research or a commercial environment. The droplet dispensing system significantly improves sample introduction into a sample handling system by increasing the efficiency, speed and controllability of forming and dispensing droplets while significantly reducing waste and contamination. Those skilled in the art will appreciate that the present invention may be implemented in a number of different applications and embodiments and is not specifically limited in its application to the particular embodiment depicted herein.

The droplet dispensing system of the present invention provides significant improvements over prior pin-based dispensing systems, which require direct contact to dispense a sample, and capillary-based dispensing systems. Capillary-based dispensing that produce droplets by means of air pressure or a remote actuator are limited to formation of large-sized droplets in the range of ten nanoliters to one microliter. Other capillary-based systems that include actuators near the tips are filled from behind the tip and generally take a long time, between ten and thirty minutes, to fill. In contrast, the droplet dispensing system of the present invention includes a filling channel and a droplet ejection actuator co-located on the end of a dispensing pin. In this manner, filling of the dispensing system is accomplished rapidly. Furthermore, the dispensing system of the present invention is capable of forming small, sub-nanoliter sized droplets.

Figure 1:
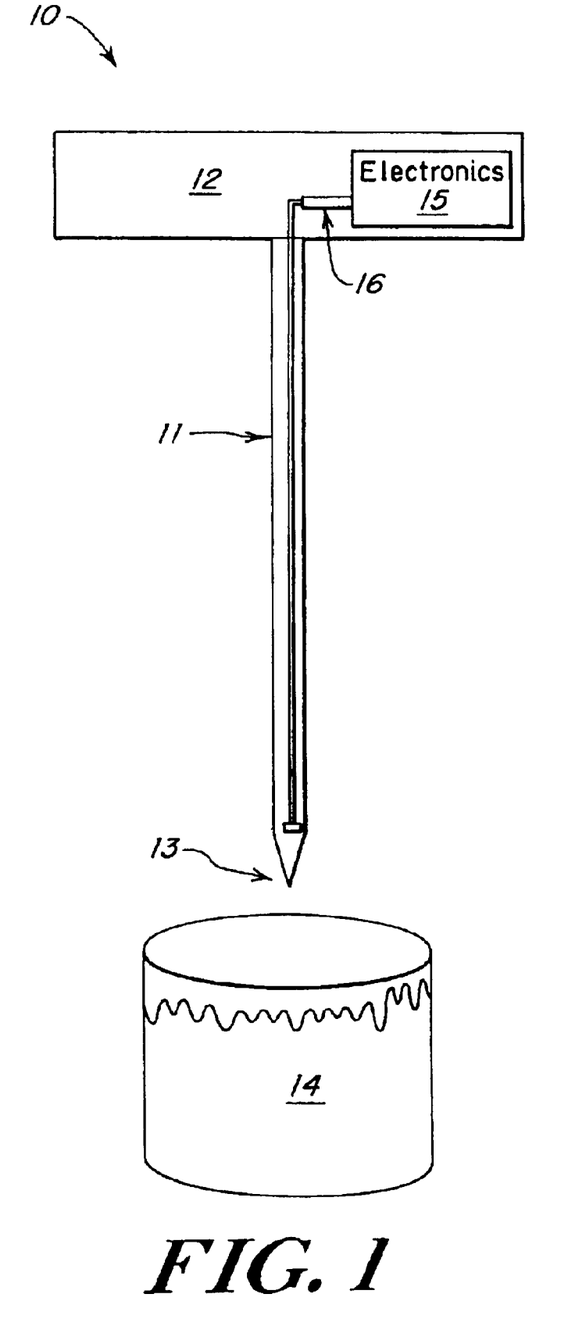
FIG. 1 is a schematic view of a droplet dispensing system according to the teachings of the present invention.

FIG. 1 illustrates the droplet dispensing system 10 of the illustrative embodiment. The droplet dispensing system comprises a dispensing pin 11 mounted in a holder 12. The droplet dispensing system 10 forms and dispenses droplets of a selected liquid sample to allow a controlled introduction of a fluid sample to a sample handling system. The sample droplets are formed and propelled ballistically from the tip 13 of the dispensing pin 11, the details of which are described below. The holder 12 can include electronics 15 comprising a control circuit for supplying a droplet ejection signal to an actuator for triggering formation and ejection of a droplet of a liquid sample from the tip 13. An electrical connector 16 provides an electrical connection between the electronics 15 and the actuator for transmitting the droplet ejection signal between the control circuit and the actuator. The details regarding the formation and ejection of droplets from the tip 13 under the control of the electronics 15 are described below. As used herein, the term holder is intended to include any structure suitable for holding or retaining in a fixed or removable and replaceable manner one or more dispensing pins.

The pin 11 of the illustrative embodiment comprises an elongated structure having a tip 13 with a diameter of about one millimeter. According to the illustrative embodiment, sample loading is accomplished by immersing the tip 13 of the dispensing pin 11 into a reservoir 14 containing the desired liquid sample. One skilled in the art will recognize that the tip 13 may have any diameter, for example, up to several millimeters, suitable for dipping into a reservoir of liquid and for holding liquid there within.

The tip 13 of the dispensing pin 11 contains a sample chamber that holds a predetermined volume of biological or chemical sample, a filling channel for filling the sample chamber, an actuator and an ejection nozzle. The tip 13 is immersed in a biochemical sample such that a predefined volume of sample fills the filling channel and the sample chamber of each pin. The droplet dispensing system 10 is then moved in proximity to a fluid interface port of a sample handling system, such as a microfluidic system or a printing substrate. An actuator disposed within the chamber is selectively activated to form and dispense droplets of the sample from the pin tip, which forms an ejection nozzle. The droplet dispensing system 10 propels droplets at a predetermined and if desired controllable velocity, and along a selected path, to introduce the liquid sample into a microfluidic system.

Figure 2:
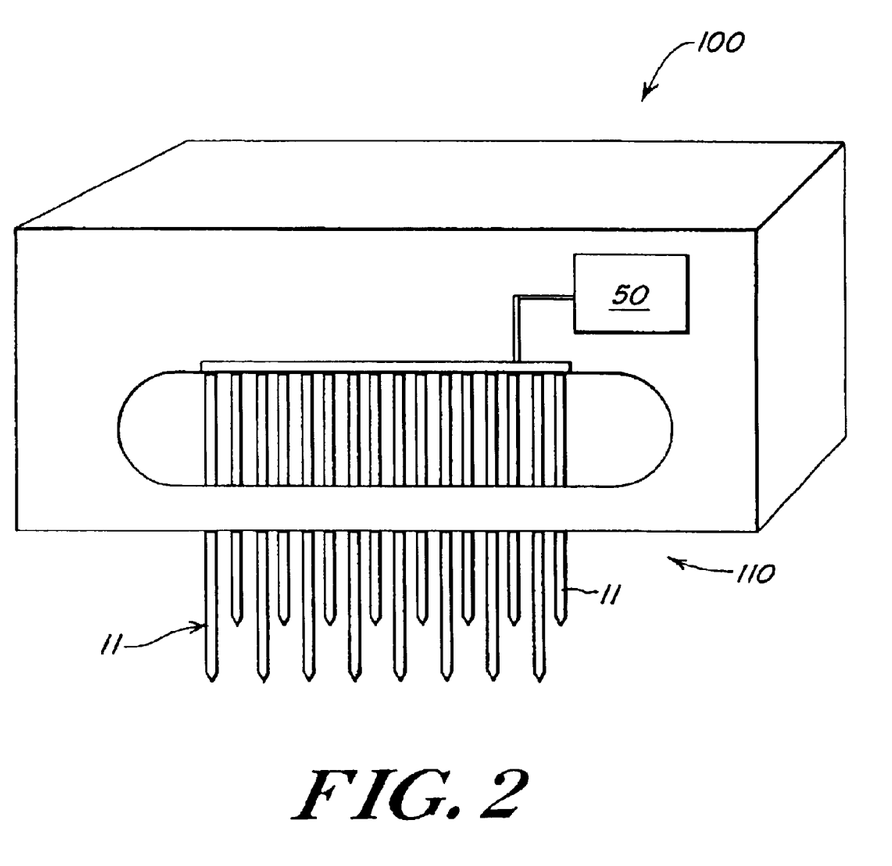
FIG. 2 is a perspective view of a droplet dispensing system according to the teachings of the present invention, comprising an array of dispensing pins connected to a holder.

According to an alternate embodiment of the invention, shown in FIG. 2, the pin dispensing system 100 can comprise an array 110 of dispensing pins 11 arranged in a holder 120 for allowing simultaneous formation and dispensing of a plurality of samples. In a pin dispensing system 100 having an array of dispensing pins 11, each dispensing pin may be individually controlled by a corresponding control circuit 150. Alternatively, a group of dispensing pins may be simultaneously controlled by common control circuit. The droplet dispensing system may comprise any suitable number of dispensing pins 11 arranged in any suitable configuration, depending on the particular application. The array of pin dispensing systems of an illustrative embodiment of the present invention may be manufactured from a substrate, such a silicon wafer, using any suitable microfabrication technique, such as photolithography.

The droplet dispensing system 10 of the illustrative embodiment of the present invention may be utilized as a spotting system for printing or discharging arrays of biochemicals, such as nucleic acid molecules or proteins, or other suitable liquid samples to a sample handing system, such as a printing substrate, titre plate, microfluidic system or device, and the like for use in proteomics, genomics, screening, diagnostics and other applications. After the pin tip 13 acquires a droplet, the pin tip 13 is moved in close proximity to a surface. The surface may comprise a solid surface or a liquid. The surface may comprise a porous structure, such as a porous membrane, or a non-porous structure, such as a microscope slide. The loaded pin or pins deposit a spot on the surface having a selected spot volume by direct contact between the pin tip 13 and the surface. According to the illustrative embodiment, the volume of the dispensed spot is significantly smaller than the volume of the acquired liquid sample, and is generally sub-nanoliter in volume, though one skilled in the art will recognize that the invention is not limited to this range.

Figure 3:
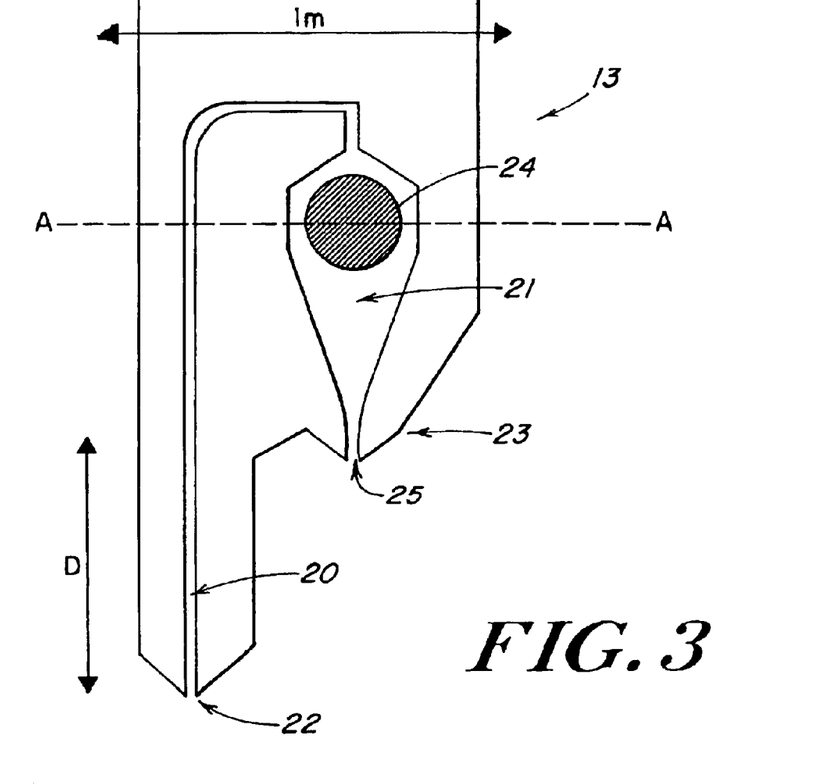
FIG. 3 is an exploded perspective view of the tip of the dispensing pin employed in the droplet dispensing system of FIG. 1.

FIG. 3 is a detailed view of the tip 13 of the dispensing pin 11 of the droplet dispensing system 10 according to a first embodiment of the invention. The tip 13 includes both a filling structure for loading the droplet dispensing system with a liquid sample and a separate droplet actuation structure for forming and ejecting droplets of the liquid sample from the tip of the dispensing pin. As shown in FIG. 3, a filling channel 20 is formed in the tip 13 for uptaking sample through an intake port 22, illustrated as a filling nozzle, from a reservoir containing a selected liquid sample. The filling channel preferably uptakes sample by employing capillary forces. The filling channel 20 communicates with a sample chamber 21 formed in the tip 13. The sample chamber 21 has a tapered end forming a droplet ejection nozzle 23. The ejection nozzle 23 includes an ejection port 25 sized and dimensioned to form droplets from a liquid sample in the sample chamber. As shown, the ejection nozzle is positioned in close proximity to and in fluid communication with the sample chamber 21. The tip further includes an actuator 24 adjacent to and contacting the sample chamber. The actuator applies a force to the sample chamber sufficient to cause formation and ejection of a liquid droplet through the ejection nozzle 23. The actuator 24 is selectively activated by the electronics in the pin holder and dispenses droplets from the ejection nozzle on demand. As illustrated, the tip 13 forms a continuous fluid path between the intake port 22, formed at the tip of the filling channel 20, and the ejection port 25, formed in the droplet ejection nozzle 23. Those of ordinary skill will readily recognize that the chamber can have any selected shape, and can be sited and dimensioned according to the particular application. Furthermore, the dispensing pin 11 may also include a plurality of sample chamber 21 formed in the tip of the pin.

Filling of the pin tip with a liquid sample is accomplished easily, flexibly and rapidly by submerging the filling nozzle 22 in a liquid sample supply. Liquid sample is drawn up the filling channel 20 and passes into the connected sample chamber 21. According to the illustrative embodiment, the filling channel 20 is sized and dimensioned so that capillary forces automatically draw the liquid sample through the filling channel 20 and into the sample chamber 21. According to an alternate embodiment, filling is effected by a pumping action provided by the actuator 24. The volume of sample that is loaded depends on the length of time that the tip is submerged in the reservoir, the size of the filling channel and chamber, and the force applied to the channel. The internal volume of the filling channel 20 and the sample chamber 21 define the maximum volume of sample that can be loaded into the tip. Those of ordinary skill will readily recognize that the intake port 20 can be formed at a number of different locations.

The droplet dispensing system 10 is capable of dispensing and discharging or propelling droplets rapidly and efficiently to a sample handling system. After the tip is filled with a liquid sample, the droplet dispensing system 10 forms and dispenses droplet of a sample liquid from the sample chamber 21 on demand by activating the actuator 24. According to the illustrative embodiment, the actuator 24 comprises a piezoelectric film affixed to a side wall of the sample chamber 21 directly adjacent to the ejection nozzle 23. The control circuit in the holder electronics produces a droplet ejection signal, which is applied through the electrical connector 16 to energize the actuator 24. When a voltage is applied to the piezoelectric film, the piezoelectric film deflects. The deflection of the piezoelectric film generates a force on the sample chamber 21, which produces and ejects a droplet from the ejection nozzle 23 though the ejection port 25. One skilled in the art will recognize that the actuator 24 is not limited to a piezoelectric actuator and that that any suitable actuator for ejecting a droplet from a nozzle may be utilized, such as the variety of actuators used in ink jet printing systems. For example, the actuator may comprise an electromechanical actuator, a magnetic actuator, a thermoelectric actuator or any suitable actuator for forming and ejecting a droplet from an ejection nozzle.

According to the illustrative embodiment, the shape of the ejection nozzle 23 and sample chamber 21, including the size and shape of the nozzle outlet port 25, determine the size and velocity of the formed droplet. The combined volume of the filling channel 20 and the sample chamber 21 determine the supply of liquid sample stored in the dispensing system with each complete filling. According to the illustrative embodiment, the interior volume of the filling channel 20 and the sample chamber 21 is between about one and about ten nanoliters. One skilled in the art will recognize that the filling channel including the intake port, and sample chamber are not limited to the illustrated configuration and that alterations and variations may be made without departing from the scope of the present invention.

The tapered droplet ejection nozzle 23 formed at the end of the sample chamber 21 is designed to accelerate and direct the flow of liquid from the sample chamber, such that droplets are propelled ballistically from the tip 13 of the dispensing pin 11. The ejection nozzle 23 and ejection port are sized and dimensioned so that liquid is generally held in by capillary forces and forced out only on demand, by calculatingly activating the actuator 24. According to the illustrative embodiment, the nozzle ejection port 25 has a diameter between about thirty and about fifty microns, resulting in a droplet having a diameter of about forty-five microns and a volume between of about thirty-five picoliters. One skilled in the art will recognize that variations of these dimensions are within the scope of the invention and that the volumes and dimensions may be varied to suit a particular application. The sample chamber 21 and filling channel 20 may be sized and dimensioned to produce between 10 and 10,000 droplets per filling, of any selected size, depending on the particular application.

According to the illustrative embodiment, the droplet ejection nozzle 23 and the intake port 22 are co-fabricated on the dispensing tip 13 to form a continuous fluid path through the dispensing pin tip 13 for loading a supply of a liquid sample and dispensing the liquid sample in the form of liquid droplets. The intake port 22 and the ejection nozzle 23 are positioned separately on the tip, such that the intake port 22 is capable of being immersed in a sample reservoir without requiring simultaneous immersion of the ejection nozzle 23. As shown, both nozzles 22 and 23 are formed in the tip of the dispensing pin, but the filling nozzle 22 extends a predetermined distance beyond the ejection nozzle 23. In this manner, the tip 13 can be loaded with a predetermined amount of liquid sample by immersing only the filling nozzle, without requiring immersion and possible contamination of the ejection nozzle as well.

Figure 4:
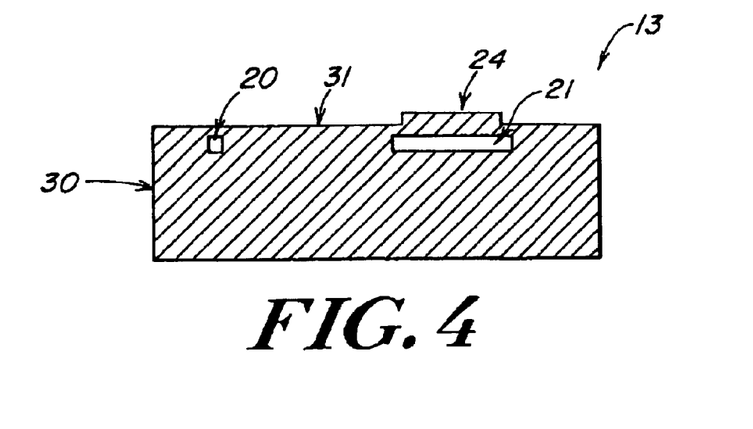
FIG. 4 is a cross-sectional view of tip of the dispensing pin of FIG. 3.

FIG. 4 is a cross-sectional view of the pin tip 13 of FIG. 3 along line A—A. As illustrated, the tip 13 comprises a silicon substrate 30. According to the illustrative embodiment, the droplet dispensing system is fabricated from a silicon wafer using a standard photolithography process. One skilled in the art will recognize that alternative materials and manufacturing techniques may be utilized. For example, the pin dispensing system may be made out of glass, plastic or any other suitable material.

To form the droplet dispensing system of the illustrative embodiment, a silicon substrate 30 is provided. The substrate is etched to form the filling channel 20, the sample chamber 21 and the ejection nozzle 23. A top layer 31 of silicon is bonded to the substrate after formation of the filling channel 20 and sample chamber 21 to cover and seal the etched channel and chamber. The actuator 24 is deposited on the exterior surface of the top layer 31, adjacent to the sample chamber 21 and in proximity to the ejection nozzle 23, such that a force produced by the actuator 24 is translated to the sample chamber 21 to form a droplet and propel the droplet from the ejection nozzle ballistically. As discussed, an electrical connector is provided to electrically connect the actuator 24 to a control circuit to allow transmission of a droplet ejection signal to the actuator 24. Those of ordinary skill will readily recognize that the tip can be manufactured and configured in a variety of different ways, such as by any conventional microfabrication technique, including photolithography.

The droplet dispensing system 10 may also be utilized with a variety of applications requiring application of a liquid sample. Once the sample is loaded in the dispensing tip 13, the dispensing pin 11 or dispensing pins are brought into proximity with a fluid interface port of a sample handling system. The droplet dispensing system of the illustrative embodiment may be utilized to form droplets of a liquid sample and introduce droplets to a microfluidic system. For example, the droplet dispensing system 10 may be utilized to supply droplets to a micro-chip having a virtual wall interface port, as described in U.S. Provisional Patent Application No. 60/299,515, entitled *Methods For Forming A Microscale Virtual Wall And Use Of Said Wall In Microfluidic Applications*, the contents of which are incorporated by reference herein. Briefly, U.S. Provisional Patent Application No. 60/299,515 describes a microfluidic system having a fluid interface port comprising an aperture sized and dimensioned to form a virtual wall in the sidewall of a microchannel. The droplet dispensing system of the illustrative embodiment may be utilized to form and propel droplets towards the virtual wall in order to introduce a liquid sample to the interior of a microchannel. Alternatively, the droplet dispensing system 10 may be utilized to introduce a liquid sample to a sample reservoir in a microfluidic system, such as a well. According to another application, the droplet dispensing system may be utilized in spotting applications for printing arrays of biochemical substances on a printing substrate, such as described in U.S. Pat. No. 6,101,946.

Figure 5:
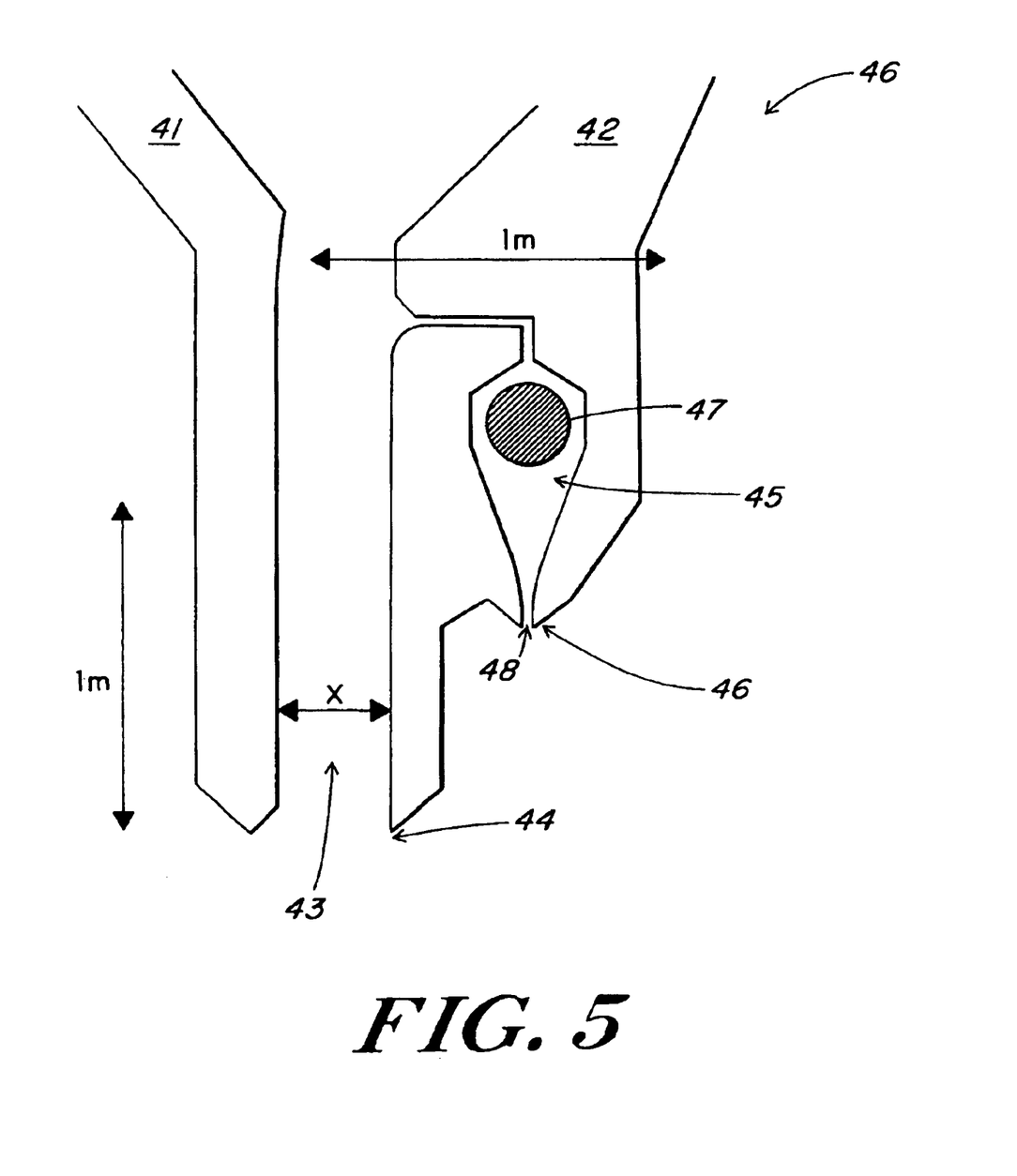
FIG. 5 is an exploded detailed view of an alternate embodiment of the droplet dispensing system, where the filling channel is formed by two interacting pin structures.

FIG. 5 is a detailed exploded view of a droplet dispensing system 40 according to an alternate embodiment of the invention, where the filling and droplet actuation mechanisms are formed in the tips of two interacting pins. As illustrated, the droplet dispensing mechanism is formed using two separately movable pins, a first pin 41 and a dispensing pin 42. The pins 41 and 42 are positioned relative to each other so as to form a filling channel 43 and filling nozzle 44 between the tips of the pins. The tip of the dispensing pin 42 includes a sample chamber 45 in fluid communication with the filling channel 43 and further includes a droplet ejection nozzle 46 formed in the tip of the pin 42 and an actuator 47 for forming droplets of a liquid sample, which are ejected from the tip of the pin 42 through an ejection port 48 in the droplet ejection nozzle 46. The separation distance D between the pins 41 and 42 is movable to increase or decrease the amount of sample acquired during filling. For example, if more sample volume per filling is desired, the separation distance is increased, thereby increasing the volume of the filling channel 43 and allowing a larger volume of liquid sample to be stored and subsequently dispensed.

The droplet dispensing system 40 of the illustrative embodiment provides significant improvements to the process of introducing a liquid sample to a sample handling system. The illustrative configuration limits dead volume between the filling channel and the sample chamber to more efficiently utilize a sample and reduce waste of the sample. The location of the actuator near the droplet ejection nozzle ensures that small droplets are formed thereby increasing the controllability and efficiency of the sample dispensing process. The flow-through design of the fluid path ensures that sample is not wasted and that the entire loaded liquid sample in the tip is utilized.

The illustrative embodiment significantly improves and enhances the ability to control the formation of droplets by allowing digital control of the quantity of dispensed sample. The droplet dispensing system forms and eject droplets on demand having a predetermined and precisely controlled volume. The volume of dispensed sample is easily modified by varying the number of droplets dispensed. For example, if a larger volume of sample is required, the actuator is activated more frequently to produce more droplets. Furthermore, the ability to produce droplets of a liquid sample on demand provides efficient utilization of resources.

The droplet dispensing system also allows dispensing of a liquid sample without requiring direct contact between the sample dispenser and a substrate or fluid interface port. The droplet dispensing system forms, propels and directs droplets with precision. The droplet dispensing system further provides rapid, easy and efficient filling and ejection of a liquid sample in controlled volumes, without requiring complicated mechanisms or machinery.

Another advantage of the droplet dispensing system of the present invention concerns the cleaning of the system after use. The flow-through design of the fluid path, including a separate intake port and ejection port, allows for cleaning solution to flush through the system, thereby reducing contaminants significantly. To clean the droplet dispensing system, the pin tip is dipped into a reservoir of cleaning solution. The actuator may be activated continuously to pump cleaning solution through the filling channel and sample chamber and out through the ejection nozzle. By flushing contaminants through the tip of the dispensing pin, the illustrative droplet dispensing system provides significant advantages over prior dispensing systems. Furthermore, the use of silicon to form the interior fluid path allows for more vigorous cleaning solutions to be utilizes without degrading the system.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

What is claimed is:

1. A sample dispensing system comprising:
   a dispensing pin having a tip and a sample chamber formed in the tip for holding a predetermined volume of sample, a sample filling channel formed in the tip and in fluid communication with the sample chamber for loading a liquid sample into the sample chamber and a droplet ejection nozzle formed separate from the filling channel in the tip and in fluid communication with the sample chamber for ejecting a droplet of the liquid sample from the sample chamber; and
   an actuator coupled to the sample chamber for forming the droplet upon activation of the actuator.

2. The sample dispensing system of claim 1, wherein the tip has a diameter between about 0.5 millimeters and about 5 millimeters.

3. The sample dispensing system of claim 2, wherein the tip has a diameter of about 1.0 millimeters.

4. The sample dispensing system of claim 1, further comprising a holder for mounting the dispensing pin.

5. The sample dispensing system of claim 4, further comprising a control circuit for activating the actuator.

6. The sample dispensing system of claim 5, further comprising an electrical connector for electrically connecting the control circuit and the actuator.

7. The sample dispensing system of claim 1, wherein the dispensing pin is formed from a silicon wafer using a microfabrication technique.

8. The sample dispensing system of claim 1, wherein the filling channel includes a filling nozzle for introducing a liquid sample to the filling channel.

9. The sample dispensing system of claim 8, wherein the filling nozzle extends beyond the ejection nozzle, such that when the tip is dipped into a reservoir, the filling nozzle is immersed in a liquid supply without immersing the ejection nozzle.

10. The sample dispensing system of claim 1, wherein the droplet ejection nozzle has an ejection port, said ejection port having a diameter between about thirty and about fifty microns.

11. The sample dispensing system of claim 1, wherein the actuator comprises a piezoelectric film affixed to a side wall of the sample chamber.

12. The sample dispensing system of claim 1, wherein the actuator comprises an electromechanical assembly for effecting ejection of a droplet from the ejection nozzle.

13. The sample dispensing system of claim 1, wherein the actuator comprises a magnetic assembly for effecting ejection of a droplet from the ejection nozzle.

14. The sample dispensing system of claim 1, wherein the actuator comprises a thermoelectric assembly for effecting ejection of a droplet from the ejection nozzle.

15. The sample dispensing system of claim 1, wherein the filling channel and the sample chamber have a combined volume of between about 1 nanoliter and about 10 nanoliters.

16. A pin for use in a system for discharging droplets, comprising:
    a tip;
    a sample chamber formed in the tip for holding a predetermined volume of sample;
    a sample filling channel formed in the tip and in fluid communication with the sample chamber for loading a liquid sample into the sample chamber; and
    a droplet ejection nozzle formed separate from the sample filling channel in the tip and in fluid communication with the sample chamber for ejecting a droplet of the liquid sample from the sample chamber.

17. The pin of claim 16, further comprising an actuator coupled to the sample chamber for forming the droplet upon activation of the actuator.

18. A liquid sample dispensing system, comprising:
    a holder;
    an array of dispensing pins connected to the holder, each dispensing pin having a tip and a sample chamber formed in the tip for holding a predetermined volume of sample, a sample filling channel formed in the tip and in fluid communication with the sample chamber for loading a liquid sample into the sample chamber and a droplet ejection nozzle formed separate from the sample filling channel in the tip in fluid communication with the sample chamber for ejecting a droplet of the liquid sample from the sample chamber; and
    an actuator coupled to the sample chamber of one or more of the dispensing pins for forming one or more droplets upon activation of the actuator.

19. A microfabricated sample dispensing system comprising:
    a dispensing pin formed from a silicon wafer using a microfabrication technique, said dispensing pin having a tip and a sample chamber formed in the tip for holding a predetermined volume of sample, a sample filling channel formed in the tip and in fluid communication with the sample chamber for loading a liquid sample into the sample chamber and a droplet ejection nozzle formed separate from the sample filling channel in the tip and in fluid communication with the sample chamber for ejecting a droplet of the liquid sample from the sample chamber; and
    an actuator coupled to the sample chamber for forming the droplet upon activation of the actuator.

20. The droplet dispensing system of claim 1, further comprising a second pin having a second tip spaced from the dispensing pin to form second filling channel between the second pin and the dispensing pin, wherein the second filling channel is in communication with the sample filling channel.

21. The droplet dispensing system of claim 20, wherein the dispensing pin and the second pin are movable relative to each other, so as to vary the size of the second filling channel.

22. The sample dispensing system of claim 20, wherein the second filling channel forms a filling nozzle for introducing a liquid sample to the second filling channel.

23. The sample dispensing system of claim 22, wherein the filling nozzle extends beyond the ejection nozzle, such that when the second pin tip and the dispensing pin tip are dipped into a reservoir, the filling nozzle is immersed in a liquid supply without immersing the ejection nozzle of the dispensing tip.

24. The sample dispensing system of claim 1, wherein the sample filling channel, the sample chamber and the droplet ejection nozzle form a substantially U-shaped fluid path through the tip.

25. The sample dispensing system of claim 1, wherein the droplet ejection nozzle is tapered.

* * * * *